United States Patent
Chang et al.

(10) Patent No.: US 7,678,336 B2
(45) Date of Patent: Mar. 16, 2010

(54) CHANNEL APPARATUS FOR FOCUSING A FLUID FLOW

(75) Inventors: Jun Keun Chang, Seocho-Ku (KR); Jun Ha Park, Suwon-Si (KR); Chanil Chung, Uiwang-Si (KR); Jung Kyung Kim, Kangnam-Ku (KR)

(73) Assignee: Digital Bio Technology, Seol (KR)

( * ) Notice: Subject to any disclaimer, the term of this patent is extended or adjusted under 35 U.S.C. 154(b) by 845 days.

(21) Appl. No.: 10/583,724

(22) PCT Filed: Dec. 17, 2004

(86) PCT No.: PCT/KR2004/003336

§ 371 (c)(1),
(2), (4) Date: Jun. 20, 2006

(87) PCT Pub. No.: WO2005/062059

PCT Pub. Date: Jul. 7, 2005

(65) Prior Publication Data

US 2008/0304720 A1    Dec. 11, 2008

(30) Foreign Application Priority Data

Dec. 22, 2003    (KR) .................... 10-2003-0094615

(51) Int. Cl.
*B01L 11/00*     (2006.01)
*G01N 33/48*     (2006.01)
*G01N 33/00*     (2006.01)
*C12Q 1/02*      (2006.01)

(52) U.S. Cl. ...................... 422/103; 436/63; 435/7.24; 435/29

(58) Field of Classification Search ................ 435/7.24, 435/29
See application file for complete search history.

(56) References Cited

U.S. PATENT DOCUMENTS 6,592,821 B1     7/2003    Wada et al.
6,994,218 B2 *   2/2006    Kawano et al. ............. 209/210
2004/0229349 A1* 11/2004   Daridon .................... 435/305.2

FOREIGN PATENT DOCUMENTS

WO    WO 98/00231 A1    1/1998
WO    WO 02/44689 A2    6/2002

OTHER PUBLICATIONS

M.S. Goel and S.L. Diamond, Blood 100 (10): 3797-3803, 2002.*
S. Usami et al., Ann. Biomed. Engineering 21: 77-83, 1993.*

* cited by examiner

*Primary Examiner*—Jill Warden
*Assistant Examiner*—Timothy G Kingan
(74) *Attorney, Agent, or Firm*—Browdy and Neimark, PLLC

(57) ABSTRACT

Disclosed is a focusing channel device which focuses fluid containing micro particles so that the micro particles flow in a line. The channel device comprises a nozzle formed by left and right walls each of which comprises an inclination surface. The cross sectional area in vertical direction decreases from the entrance of the nozzle toward the exit of the nozzle. The shape of cross sectional view in horizontal direction is asymmetric for the central line in the length direction. Using the focus channel device of the invention, the micro particles in the fluid are not combined with each other and passed through the channel one by one. Thus, blockage of the channel or combination and movement of two particles together does not occur.

15 Claims, 8 Drawing Sheets

Time

CHANNEL APPARATUS FOR FOCUSING A FLUID FLOW

TECHNICAL FIELD

The invention relates to a focusing channel device which focuses fluid containing micro particles so that the micro particles flow in a line. The channel device comprises a nozzle formed by left wall and right wall each of which comprises an inclination surface. The cross sectional area in vertical direction decreases from the entrance of the nozzle toward the exit of the nozzle. The shape of cross sectional view in horizontal direction is asymmetric for the central line in the length direction.

BACKGROUND ART

Currently, researches and commercialization of a point of care (POC) and a lab-on-a-chip (LOC) (which means a laboratory on a chip and is a technology for diagnosing various diseases in a small chip at a time) are actively carried out in the field of bio-industry. The LOC makes the experiment equipments used in various field such as, biology, medical science, pharmacology, and so on to be embodied on a single plastic micro-chip. Using the micro-chip, information of every single cells or particles existing in body fluids or solutions could be obtained and examined.

In order to obtain information on cells or particles, cells (particles) should be flowed in a line in the channel. To make it possible, the process of focusing the fluid which contains the cells (particles) to pass through only a fixed area is necessary.

Conventional focusing channel has a nozzle the width of which is narrowed in symmetry on both right and left sides of the channel. Due to the symmetry of both sides of the channel, cells (particles) entering the symmetrically narrowing channel simultaneously block the focusing channel, or two cells (particles) are combined into one cell and flow as one cell. Thus, bottleneck phenomenon occurs as such.

FIG. 1 is a photograph of red blood cells flowing in a conventional focusing channel composed of symmetric fixed walls. In FIG. 1, the oval mark indicates a point where two red blood cells enter the focusing channel at the same time and the bottleneck phenomenon occurs due to the symmetric shape of left and right walls in the focusing channel.

FIG. 2 is a photograph of red blood cells flowing in a conventional focusing channel composed of symmetric fluid walls. In FIG. 2, two red blood cells also enter the focusing channel at the same time and the bottleneck phenomenon occurs due to the symmetric shape of left and right fluid walls in the focusing channel similarly to the case of FIG. 1.

These situations of blockage and combination of two cells (particles) into one in the focusing channel may cause an error in data analysis, and eventually deteriorate efficiency of the analysis devices. For instance, in the focusing channel used in device for diagnosis of cancer or diabetes by examining the flow velocity of red blood cells, above defects may cause the slowdown of flow velocity. Thus, it may be impossible to diagnose such disease precisely.

The 'fixed wall' used herein means an actual solid wall formed on a plastic micro-chip in designing and manufacturing of the micro-chip.

The term 'fluid wall' means a wall of fluid state. It does not form an actual wall in the micro chip. However, when flowing the fluids containing particles to be observed in the channel, buffer solution is also flowed in the left and right sides of the flowing fluids, and thereby the buffer solution serves as a wall. FIG. 3 shows a focusing process for fluids using the fluid wall.

DISCLOSURE OF INVENTION

The invention is suggested to solve the bottleneck phenomenon above mentioned. The inventors have confirmed that the above defects are solved if right and left sides of focusing channel are formed asymmetrically.

Therefore, the object of the invention is to provide a focusing channel device for flowing a fluid without occurrence of the bottleneck phenomenon.

Further, other object of the invention is to provide a micro particle analysis device using this focusing channel device.

The invention relates to a focusing channel device wherein both sides of the channel are formed asymmetrically.

More specifically, the invention relates to a focusing channel device which focuses fluid containing micro particles (e.g., blood cells, or bacteria) to flow through only a predetermined area so that the micro particles flow in a line, comprising a nozzle formed by left wall and right wall each of which comprises an inclination surface, wherein the cross sectional area in vertical direction decreases from the entrance of the nozzle toward the exit of the nozzle, and the shape of cross sectional view in horizontal direction is asymmetric for the central line in the length direction.

The asymmetric left and right walls may be achieved by forming the inclination surface of one of the left or right wall, which forms the nozzle, closer to the entrance of the channel than the inclination surface of other wall.

It is preferable that the inclination surface of one of left or right wall is formed closer to the entrance of the channel than the inclination surface of other wall by the diameter of particle. For instance, in order to observe red blood cells, the asymmetric left and right walls may be achieved by forming the inclination surface of the left wall closer to the entrance of the channel than the inclination surface of the right wall by 7 micrometer.

In the invention, the left and the right wall may be fixed walls formed by solid material, or fluid walls formed by a flow of other fluids.

In the invention, upper wall and lower bottom wall of the channel may be formed parallel. Otherwise, similarly to the case of the asymmetric left and right wall, the inclination surfaces of the upper wall and lower bottom wall may also be formed asymmetrically.

In case that the upper wall and lower bottom wall are formed parallel, several micro particles may pass simultaneously in vertical direction. However, if the channel is manufactured at an appropriate height, the micro particles in the channel may pass one by one in the vertical direction. For instance, if the channel device for analysis of red blood cells is manufactured to have a height of about 7 micrometer which is a diameter of red blood cell, the red blood cell may pass one by one in the vertical direction in the channel.

The invention further relates to a micro particle analysis device comprising the focusing channel as mentioned above; a photographing means by irradiating light on the micro particles flowing in a line in the focusing channel and photographing the micro particles; and an image analysis means for analyzing the photographed image of the micro particles.

BRIEF DESCRIPTION OF DRAWINGS

A more complete appreciation of the invention, and many of the attendant advantages thereof, will be readily apparent as the same becomes better understood by reference to the following detailed description when considered in conjunction with the accompanying drawings in which the reference symbols indicate the same or similar components, wherein.

Figure 1:
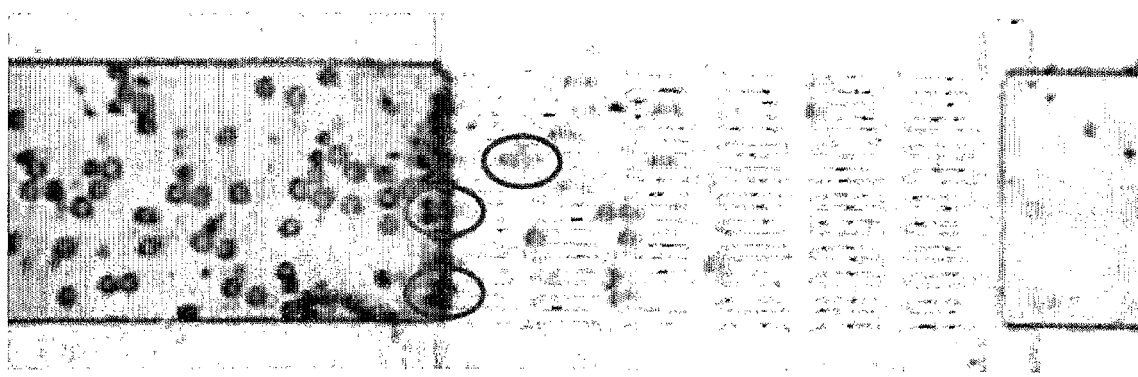
FIG. 1 is a photograph of red blood cells flowing in a conventional focusing channel composed of symmetric fixed walls.
Figure 2:
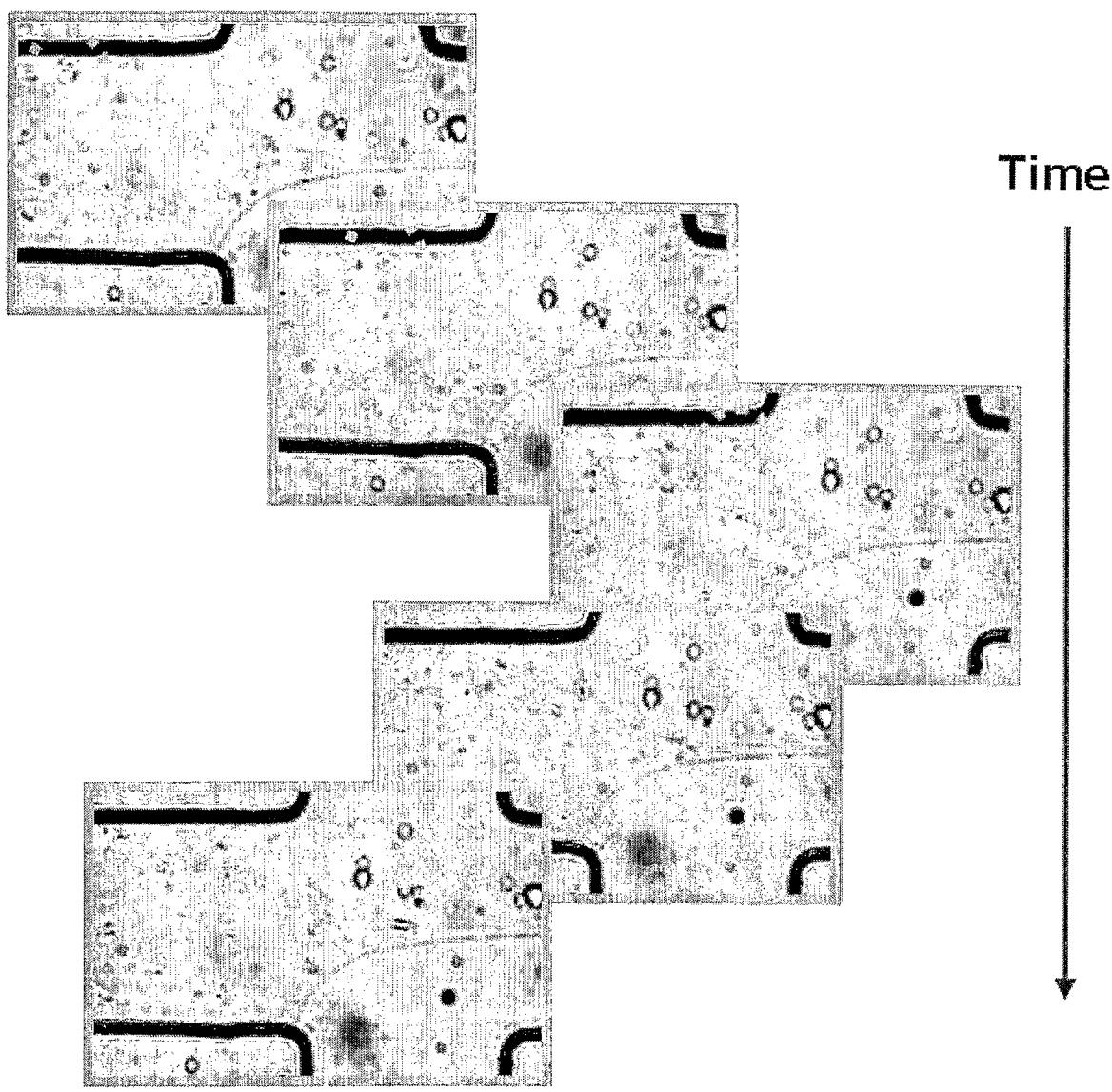
FIG. 2 is a photograph of red blood cells flowing in a conventional focusing to channel composed of symmetric fluid walls.
Figure 3:
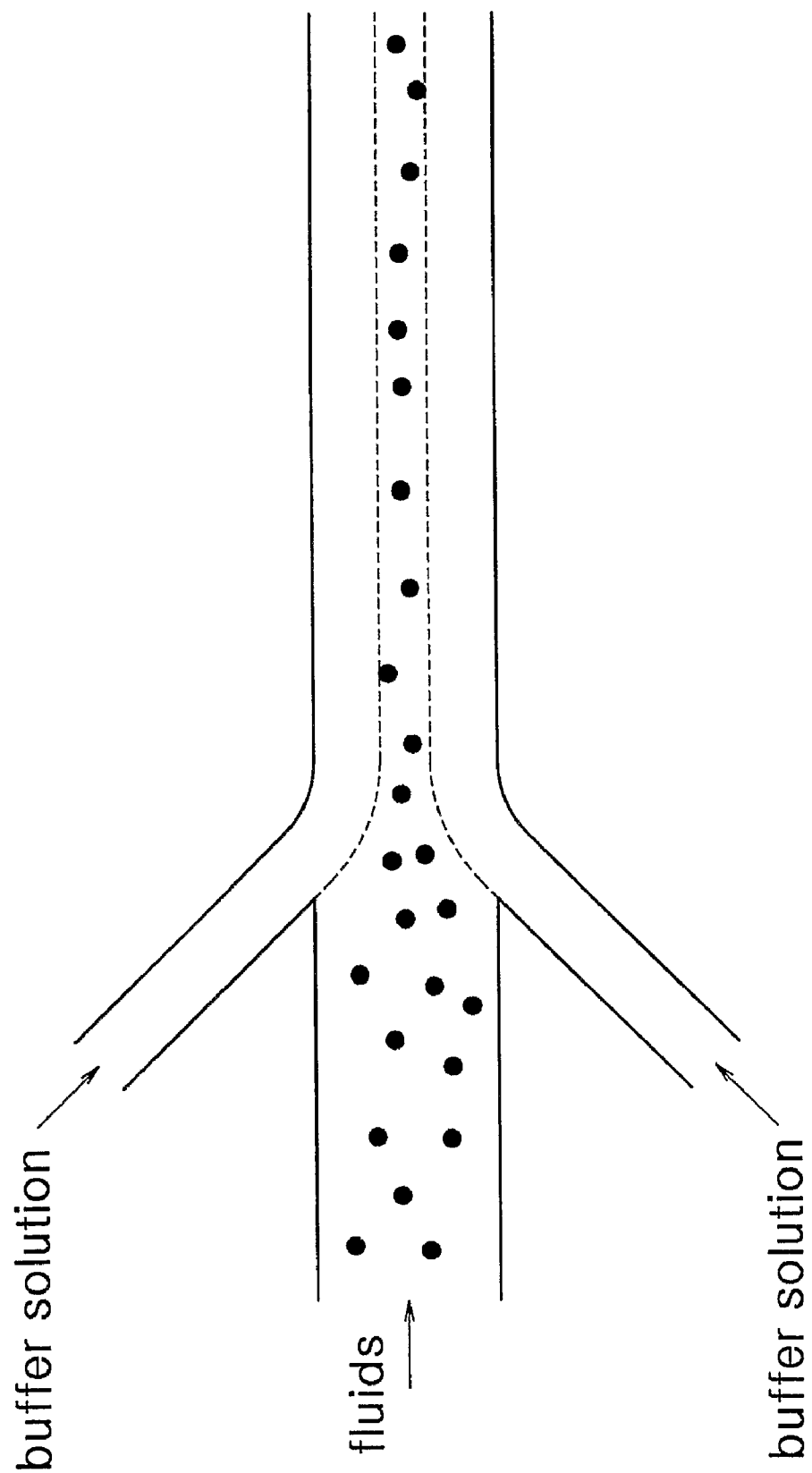
FIG. 3 illustrates fluid walls.

DESCRIPTION OF REFERENCE NUMERALS
FOR IMPORTANT PART OF THE DRAWINGS

10: left wall
20: right wall
30: nozzle
A: inclination surface of the left wall
B: inclination surface of the right wall
L: difference between the positions of both inclination surfaces
H: height of the channel

BEST MODE FOR CARRYING OUT THE INVENTION

Hereinafter, preferred embodiments of the present invention will be described with reference to the accompanying drawings. In the following description of the present invention, a detailed description of known functions and configurations incorporated herein will be omitted when it may make the subject matter of the present invention rather unclear.

Figure 4:
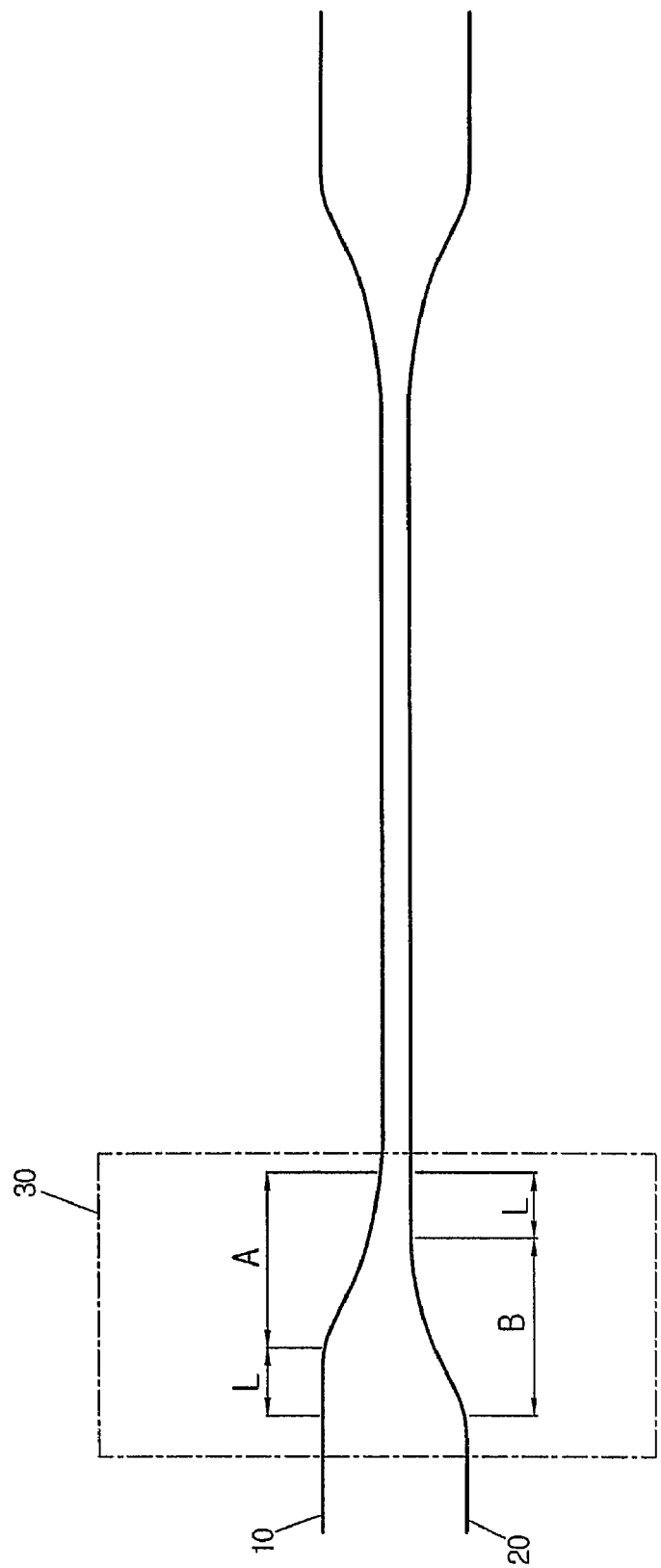
FIGS. 4 and 5 are a cross sectional view and a perspective view of the focusing channel with fixed walls according to the invention, respectively.
Figure 5:
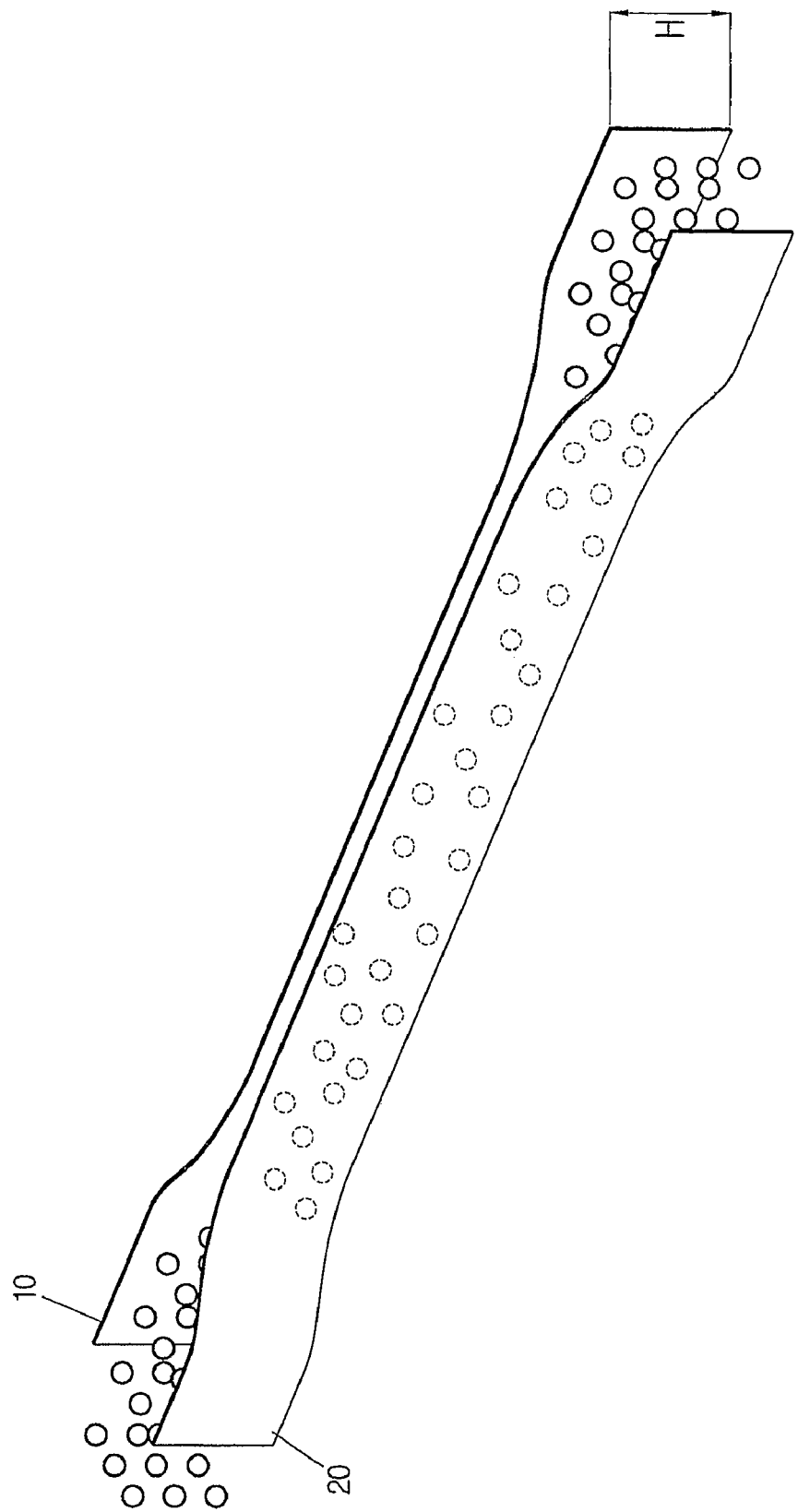

FIGS. 4 and 5 are a cross-sectional view and a perspective view of the focusing channel device according to the invention, respectively.

The focusing channel device of the invention focuses fluids containing micro particles (e.g., bead, blood cells or bacteria) to flow through only a predetermined area so that the micro particles flow in a line.

The device of the invention comprises a nozzle (30) which is formed by a left wall (10) comprising an inclination surface (A) and a right wall (20) comprising an inclination surface (B). The cross sectional area of the nozzle (30) in vertical direction is decreasing from the entrance of the nozzle toward the exit of the nozzle.

The shape of cross sectional view of the channel device in horizontal direction, especially at the nozzle (30) is asymmetric for the central line in the length direction. In FIGS. 4 and 5, the inclination surface (B) of the right wall (20) is formed closer to the entrance of the channel device than the inclination surface (A) of the left wall (10) by distance L. The distance L between the inclination surfaces A and B may be set as appropriate. It is preferable that the distance L is set to be same with the diameter of the micro particle to be observed.

The micro particles are passed one by one in the width direction of the channel. However, in the vertical direction, one or more micro particles may pass together simultaneously. If the channel is manufactured at an appropriate height (e.g., not less than the diameter of the micro particle and not more than twice of the diameter), the particles may also pass through one by one in the vertical direction.

The channel device of the invention may be easily manufactured with plastic materials.

Figure 6:
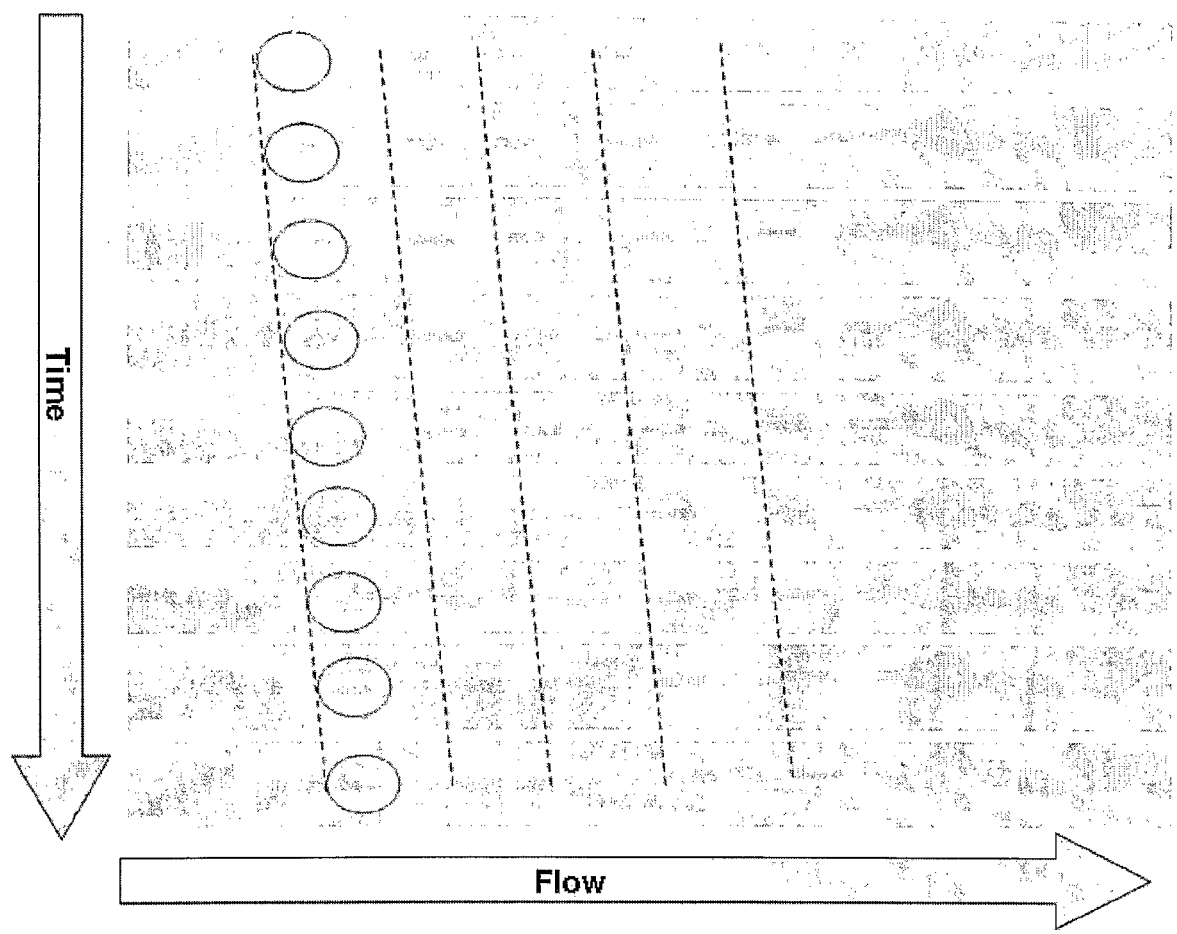
FIGS. 6 and 7 are photographs of red blood cells taken by a device for examining red blood cells comprising a focusing channel according to the invention.
Figure 7:
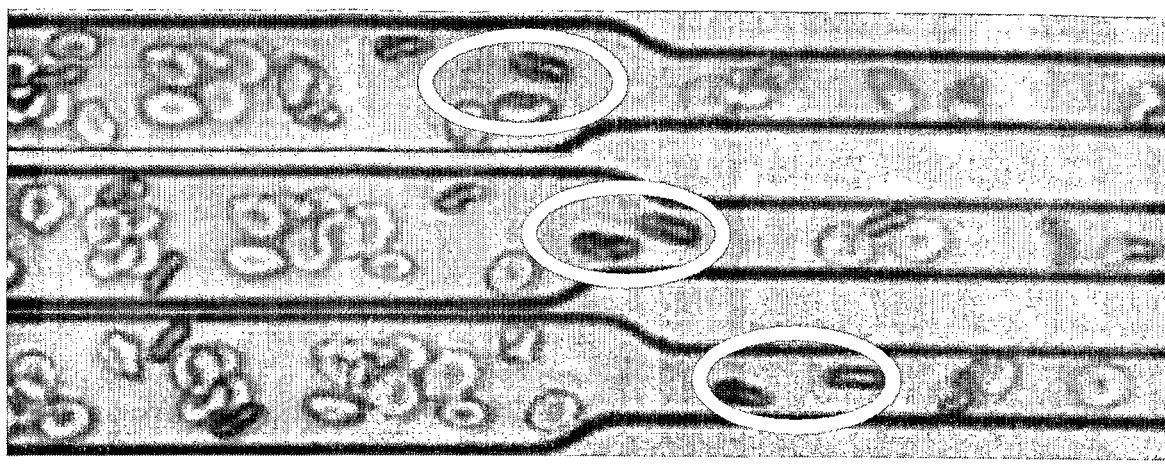

FIGS. 6 and 7 are photographs of deformed red blood cells flowing in the focusing channel which is applied to a deformation measurement device for red blood cells. It shows that due to the asymmetric shape of the left and right walls in the focusing channel, bottleneck phenomenon does not occur, and space between each particles are regular while they progress.

Figure 8:
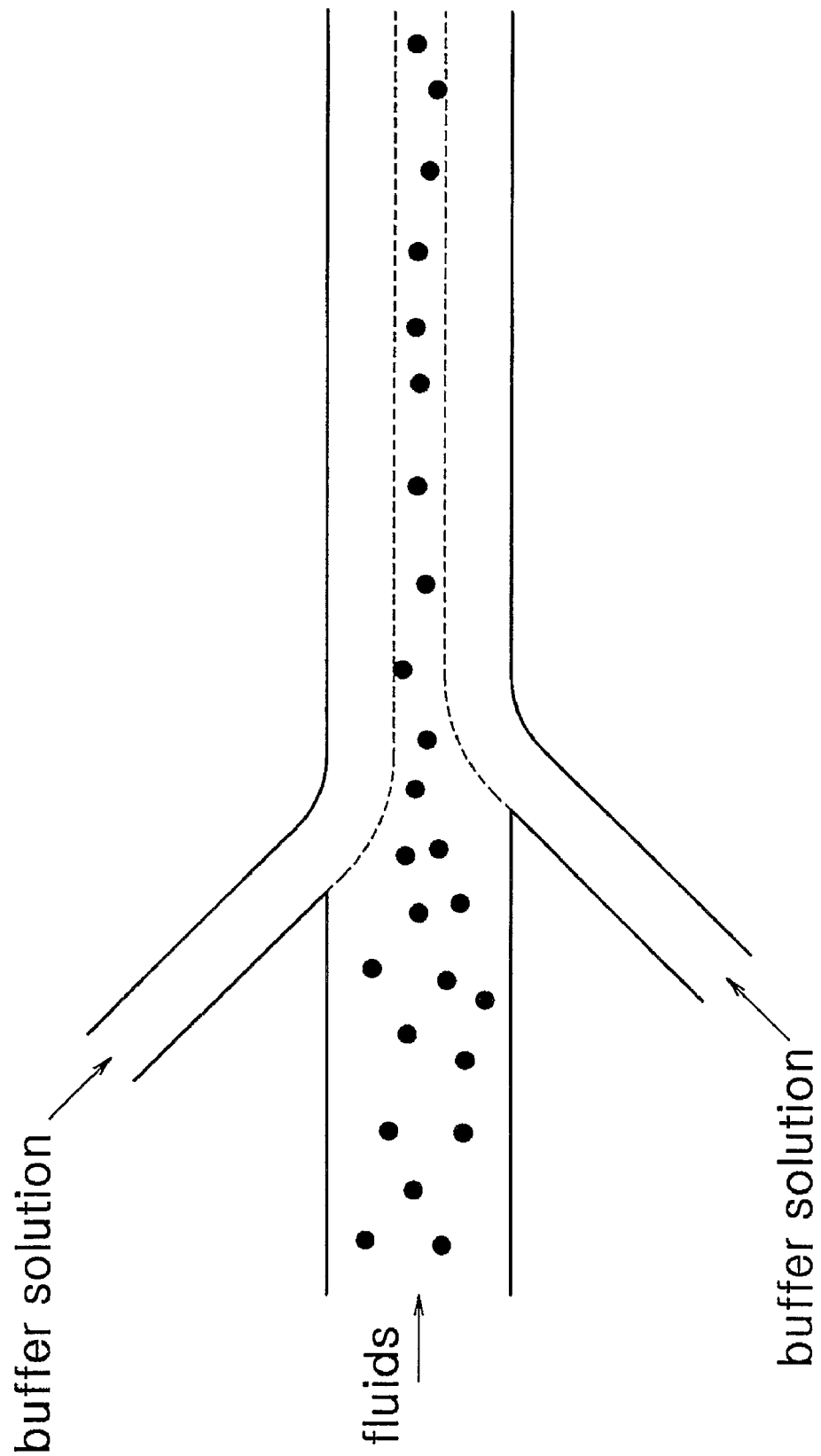
FIG. 8 is a cross-sectional view of the focusing channel with fluid walls according to the invention.

In case of using fluid walls, asymmetry of the side walls is achieved by adjusting the position where the buffer solution is injected at both sides of the fluids containing the micro particles or the amount of the injected buffer solution. FIG. 8 illustrates the focusing channel with the asymmetric fluid walls. As shown in FIG. 8, the inflow position for the buffer fluid on one side is closer to the entrance of the channel device than that on the other side. Thus, the asymmetric fluid walls is formed.

INDUSTRIAL APPLICABILITY

Using the focus channel device of the invention, the micro particles in the fluid are not combined with each other and passed through the channel one by one. Thus, blockage of the channel or combination and movement of several particles together does not occur. Therefore, precise results can be obtained when observing particles using the device of the invention.

What is claimed is:

1. A focusing channel device which focuses fluid containing micro particles to flow through only a predetermined area so that the micro particles flow in a line, the focusing channel device comprising:
a nozzle formed by a left wall and a right wall each of which comprises an inclination surface,
the cross sectional area of the nozzle in vertical direction decreases from the entrance of the nozzle toward the exit of the nozzle, and
the cross sectional view of the channel in horizontal direction has a shape that is asymmetric for the central line in the length direction,
wherein the inclination surface of one of the left wall or the right wall, which forms the nozzle, is placed on the entrance of the channel device and the inclination surface of the other wall is placed at a distance L from the entrance of the channel device, wherein the distance L is set by a factor of a diameter of the micro particle.

2. The focusing channel device according to claim 1, wherein the left and right walls are fixed walls formed by solid material.

3. The focusing channel device according to claim 1, wherein the left and right walls are fluid walls formed by flow of other fluids.

4. The focusing channel device according to claim 1, wherein upper wall and lower bottom wall are formed parallel, and are fixed walls.

5. The focusing channel device according to claim 1, wherein the height of the nozzle of the channel is decreasing from the entrance of the nozzle toward the exit of the nozzle by the inclination surfaces of the upper wall and lower bottom wall, and the inclination surfaces of the upper wall and lower bottom walls are formed asymmetrically.

6. The focusing channel device according to claim 1, wherein the height of the channel is not less than the diameter of the micro particle.

7. The focusing channel device according to claim 1, wherein the micro particle is a bead, a cell or a bacterium.

8. A micro particle analysis device comprising:

the focusing channel device according to claim 1;

a photographing means for irradiating light on the micro particles flowing in a line in the focusing channel device and photographing the micro particles; and an image analysis means for analyzing the photographed image of the micro particles.

9. The micro particle analysis device according to claim 8, wherein the left and right walls are fixed walls formed by solid material.

10. The micro particle analysis device according to claim 8, wherein the left and right walls are fluid walls formed by flow of other fluids.

11. The micro particle analysis device according to claim 8, wherein upper wall and lower bottom wall are formed parallel, and are fixed walls.

12. The micro particle analysis device according to claim 8, wherein the height of the nozzle of the channel is decreasing from the entrance of the nozzle toward the exit of the nozzle by the inclination surfaces of the upper wall and lower bottom wall, and the inclination surfaces of the upper wall and lower bottom walls are formed asymmetrically.

13. The micro particle analysis device according to claim 8, wherein the height of the channel is not less than the diameter of the micro particle.

14. The micro particle analysis device according to claim 8, wherein the micro particle is a bead, a cell or a bacterium.

15. The focusing channel device according to claim 1, wherein the inclination surface of one of the left wall or the right wall is closer to the entrance of the channel device than the inclination surface of the other wall by 7 micrometers.

\* \* \* \* \*